United States Patent [19]
Rootzen et al.

[11] Patent Number: 5,461,435
[45] Date of Patent: Oct. 24, 1995

[54] METHOD AND AN APPARATUS FOR CHECKING THE THRESHOLDS OF A SUBJECT'S PERCEPTION OF VISUAL STIMULI

[76] Inventors: Holger Rootzen, Olshogsvagen 6, S-223 60 Lund; Anders Heijl, Danska vagen 62,, S-226 39 Lund; Jonny Olsson, Fasanvagen 5A, S-227 31 Lund, all of Sweden

[21] Appl. No.: 57,671

[22] Filed: May 5, 1993

[51] Int. Cl.$^6$ .................................................. A61B 3/02
[52] U.S. Cl. ........................ 351/226; 351/222; 351/224
[58] Field of Search ................................ 351/224, 226, 351/225, 222, 223, 246

[56] References Cited

U.S. PATENT DOCUMENTS

| | | |
|---|---|---|
| 3,883,234 | 5/1975 | Lynn et al. . |
| 4,334,738 | 6/1982 | Seckinger . |
| 4,429,961 | 2/1984 | Sheingorn . |
| 4,697,895 | 10/1987 | Sekiguchi et al. . |
| 4,927,259 | 5/1990 | Weber . |
| 5,050,983 | 9/1991 | Johnson et al. . |

FOREIGN PATENT DOCUMENTS

WO85/02103  5/1985  WIPO .

OTHER PUBLICATIONS

Olsson, Jonny et al, "An Image Model For Quantal Response Analysis in Perimetry", Center for Stochastic Processes, University of North Carolina, Technical Report No. 355, pp. 1–26, Nov. 1991.

Jonny Olsson, "Statistics in Perimetry", Department of Mathematical Statistics, Lund University, 1991, pp. 1–39 and Appendices H–K.

*Primary Examiner*—William L. Sikes
*Assistant Examiner*—Hung Xuan Dang
*Attorney, Agent, or Firm*—Burns, Doane, Swecker & Mathis

[57] ABSTRACT

In a method of checking the threshold values of a subject's perception of visual stimuli, for each one of a selection of test series, the estimated error of a threshold value estimate of the test series is used to judge whether the test series is to be continued or not. This means that a test series may be discontinued as soon as the threshold value thereof can be determined with acceptable accuracy. Preferably, a posterior probability function is used for estimating the error. An apparatus for carrying out the method includes a control unit operating according to the method.

20 Claims, 3 Drawing Sheets

METHOD AND AN APPARATUS FOR CHECKING THE THRESHOLDS OF A SUBJECT'S PERCEPTION OF VISUAL STIMULI

FIELD OF THE INVENTION

The present invention relates to visual testing, and in particular to an improved test strategy to be used in visual testing. The invention also relates to an improved apparatus for carrying out the test strategy.

BACKGROUND OF THE INVENTION

Perimetry is a very important and common test in clinical eye care, second only to the simple determination of visual acuity. It is used for examining the range and the sensitivity of a subject's visual field, e.g. in connection with diagnosis and treatment of glaucoma, for testing for neurological diseases, in mass screening etc.

In static threshold perimetry, the limit or threshold of a subject's light perception at a number of discrete locations in the visual field is determined. The test is conducted by means of a computerized perimeter, typically in the following way: the patient is seated in front of a perimeter and asked to look steadily at a centrally placed fixation target, e.g. on a screen or in a hemispherical bowl. Visual stimuli are presented successively with different intensities and at different locations. The patient is asked to press a response button every time he perceives a stimulus, whether close to or distant from the fixation target, whether faint or strong.

There are different strategies for selecting test locations and intensities of the stimuli presented at these test locations in order to establish a patient's threshold for perception of light. In one common method, a stimulus is shown having an intensity close to the expected threshold value at each test location concerned. If the patient does not respond to the stimulus, the intensity of the subsequently presented stimuli is thereafter increased stepwise until a response is received from the patient, i.e. until a stimulus is seen. The first intensity level at which a response is received can be defined as the threshold of the test location concerned. The precision of the test can be increased by reversing the test process when the first response is received, and by continuing it in smaller steps with decreasing intensities until the first unseen stimulus is encountered. The threshold can then be defined as the average intensity level of the last seen stimulus and the first unseen stimulus. If, on the other hand, the patient responds to the first stimulus, the intensity is decreased stepwise until no response is received, whereupon the test procedure is reversed.

The test locations are usually tested in random order, a stimulus at a first test location being followed by a stimulus at another test location etc., and the next stimulus for the first test locations being not presented until after several subsequent stimulus presentations.

The above method of presenting series of visual stimuli with alternately increasing and decreasing intensities is called the staircase method.

In the staircase method, the intensity steps between stimuli of increasing/decreasing intensities are constant, at least between reversals. A variant hereof is the Robbins-Monroe method where the steps between successive stimuli are gradually decreased.

Another method for determining threshold values is the Modified Binary Search (MOBS), according to which a stimulus with a selected intensity close to the expected threshold value of the subject is presented. If the stimulus is seen, its intensity value is regarded as the upper threshold boundary and, if it is not seen, as the lower threshold boundary. The intensity range is then divided into a series of increasingly smaller half-intervals until the upper and lower treshold boundaries are within a defined range.

When the threshold values for all the test locations in the visual field have been determined, they are often compared with normal, previously determined threshold values for patients of the same age to establish whether there are any deviations from normal, or with previous values for the same eye of the patient to establish whether a disease under observation has progressed or receded.

One problem inherent in static threshold perimetry is that this technique is time-consuming. As described above, several stimuli of different intensities are presented at each test location on the screen. Since 50–100 test points are usually examined, one test consists of several hundred stimulus presentations. Typically, the time required for a complete static threshold perimetry test is about 10–20 minutes per eye. The test is very tiring, which may affect the test accuracy.

Furthermore, even though the test procedure is computerized, an operator must usually be present during the test to ensure that the patient maintains fixation, to encourage him and to answer any questions he may have.

Another problem of static threshold perimetry is the assessment of the responses from the patients. After each presentation of a stimulus, the perimeter waits for a response during at most a predetermined time period. If no response is received during the predetermined time period, the stimulus has usually not been seen, and if a response is received, the stimulus has usually been seen. However, it is well-known that patients sometimes press the button without having seen any stimulus at all, and they sometimes fail to press it despite having seen the stimulus. These kinds of responses are called false positive responses and false negative responses, respectively. It goes without saying that they affect the accuracy of the threshold determination and, hence, have an essential impact on the choice of test strategy.

The frequency of false positive responses may be examined by false positive catch trials. The perimeter acts as when displaying a stimulus but without showing one, and registers whether the patient responds or not. The frequency of false negative responses may be examined by false negative catch trials. A strong, supraliminal stimulus is presented at a point where the threshold has already been measured, and the perimeter registers whether the patient responds or not. Often 20–30 catch trials are presented during a test.

Many suggestions have been made for shortening the total time required for performing static threshold perimetry by reducing the number of presentations of stimuli.

Heijl A, Krakau CET: An automatic perimeter for glaucoma visual field screening and control; Albrecht v. Graefes Arch. Clin exp. Ophthalmol 197:13–22, 1975, and U.S. Pat. No. 4,334,738 describe methods for better selecting the intensity level for the first stimulus presented at each test point, whereby the number of presentations of stimuli required for arriving at a threshold value can be reduced.

U.S. Pat. No. 4,927,259 discloses a test strategy which is based on the above-mentioned staircase method, but where the steps of the staircase are logarithmic instead of constant.

U.S. Pat. No. 5,050,983 discloses a test strategy, where some test points are fully tested by the staircase or MOBS method and the remaining test points are tested by just a few stimulus presentations. First, the threshold values of a few seed points are determined by the staircase method or the modified binary search method. Then, the expected threshold values of the neighbor non-seed points are determined. These expected threshold values are tested in a first phase by presenting a visual stimulus, the intensity of which is either decidedly below or decidedly above the expected threshold value in each of the neighbor points, and by checking that the response is in accordance with the expected response ("not seen" and "seen", respectively). Then, the agreement between the expected response and the actual response for each test point is compared with that of its neighbors, and on the basis of this comparison, the neighbor agreement between each point in the field and its nearest neighbors is classified into a "discrepancy", "low-confidence" or "high-confidence" category. The expected threshold value of test points in the low-confidence category is then adjusted for better neighbor agreement.

In a second phase of the method, a further visual stimulus is presented at each non-seed point. The test points which in the first phase were tested with a visual stimulus above the expected threshold value are now tested with a visual stimulus below the expected threshold value, and vice versa. For test points in the "high-confidence" category, the interval between the stimulus intensity and the expected threshold is decreased. Then, the agreement between the responses and the expected responses is determined and compared with that of its neighbors in the same manner as in the first phase. The testing of test points which after the second phase are in the "high-confidence" category is terminated. The expected threshold values of test points in the "low confidence" category are adjusted for better neighbor agreement, whereupon these test points are tested anew in accordance with the first phase. Test points in the "discrepancy" category are retested by the staircase method or the MOBS method.

Moreover, a doctoral dissertation "Statistics in perimetry", Department of Mathematical Statistics, Lund, 1991, by Jonny Olsson, describes the use of posterior probability functions to estimate threshold values after a conventional static threshold perimetry test has been carried out.

SUMMARY OF THE INVENTION

One object of the present invention is to provide an improved test strategy for checking the threshold values of a subject's perception of visual stimuli.

Another object of the invention is to provide an apparatus for carrying the test strategy into effect.

A further object of the invention is to provide a method and an apparatus which permit shortening the time for checking the threshold values of a subject's perception of visual stimuli without increasing the measurement error.

These objects are achieved by a method according to the appended method claims.

According to the method, an estimation is made, for each one of a selection of the test series, of the value of the error of a threshold value estimate, and the value of the error is used for deciding whether the test series should be continued or not. In other words, by using the error of the threshold value estimate, the testing of a point can be discontinued as soon as the threshold value can be determined with acceptable accuracy. In comparison with the known staircase method, this means that testing can be interrupted in certain cases after considerably fewer stimulus presentations, but that it may sometimes use more stimulus presentations, then giving a better estimation of the threshold value. Moreover, the method confers the advantage that the error becomes more evenly distributed over the test series. As compared with clinically employed tests of similar type, the total number of stimulus presentations in a static threshold perimetry test can be reduced by 10–20%.

The above-mentioned objects are also achieved by an apparatus according to the appended apparatus claims.

The present invention is applicable to different types of visual tests, e.g. in perimetry, both in screening where only one or a few stimuli are presented for each test location to check whether the threshold value thereof is normal or not, and whether the location is to be more thoroughly tested or not, and in static or kinetic threshold perimetry, where the threshold values of different locations are actually determined.

The present invention may confer the same advantages also in other visual tests where the patient is instructed to respond when perceiving a stimulus, and not to respond when not perceiving it. Examples of such tests are computerized, central or peripheral visual acuity testing, or determination of contrast sensitivity. In these kinds of tests, all stimuli may be presented in one location only, but the stimuli may have different appearances and each threshold value may be related to stimuli of a specific appearance.

Stimuli may be simple and well-defined white circular stimuli against an even, white background, which is typical in today's clinical perimetry. Stimuli may, however, also be of almost any other character, e.g. colored, composed of high- or low-contrast gratings or moving bars of light, consisting of multiple components or even complex images.

A test series as defined in this application includes one or more stimuli, which either have a specific test location in common, or have a specific appearance or any other parameter in common, the threshold value of which is to be tested.

In screening tests, all presented stimuli may be of the same strength, but in threshold tests, visual stimuli of different strengths are presented to check or determine the threshold values of the subject under test. The strength of the stimuli is often the intensity of the stimuli, but may as well be the color, the size, the color saturation, the spatial frequency, the flicker frequency or any other parameter thereof which may be varied.

The above-mentioned and other objects and features of the present invention will become more apparent from a consideration of the following detailed description in conjunction with the accompanying drawings.

DESCRIPTION OF THE PREFERRED EMBODIMENT

Figure 1:
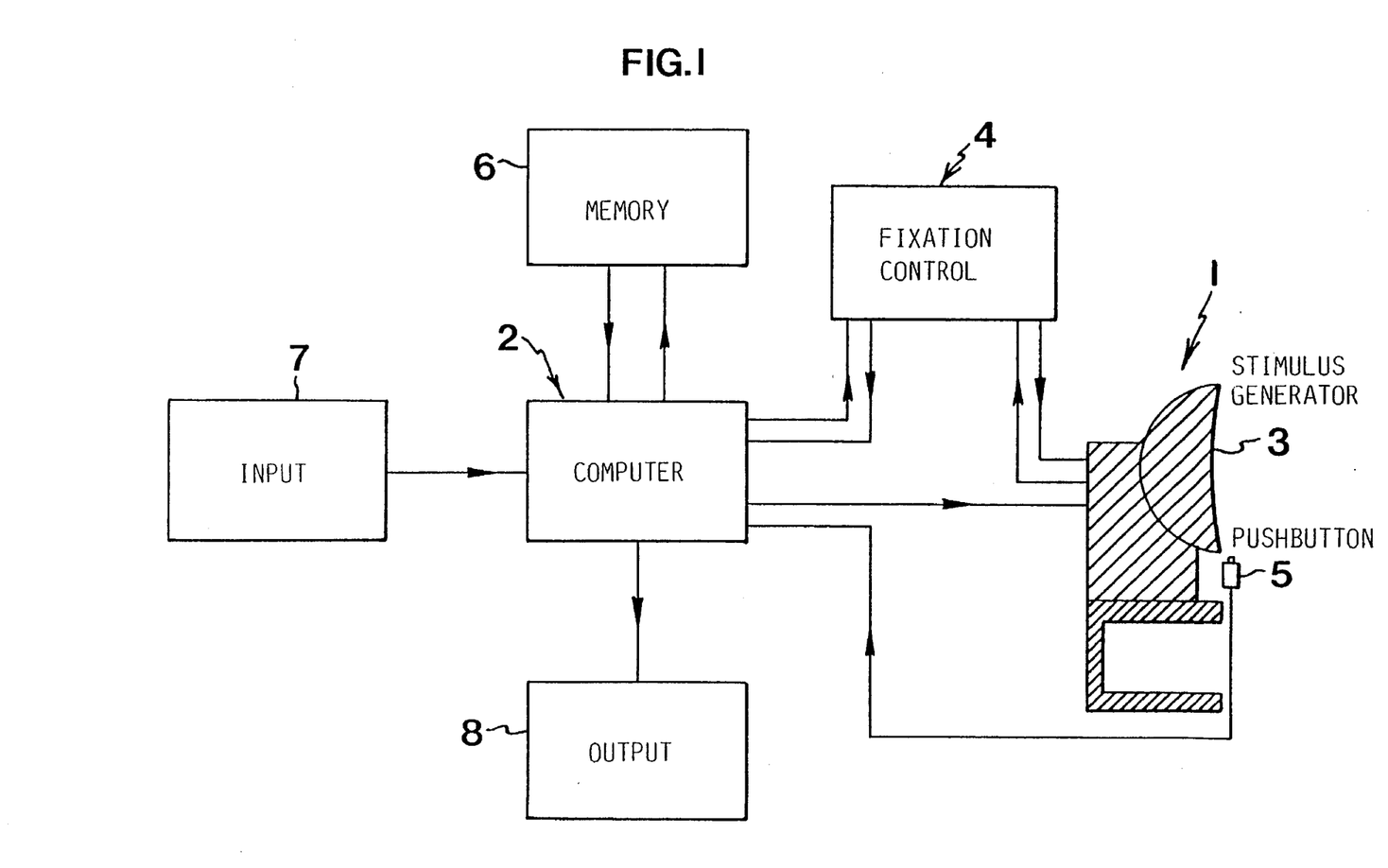
FIG. 1 schematically shows a computerized perimeter.

FIG. 1 shows schematically, partly in the form of a block diagram, the design of a computerized perimeter, by means of which the method of the invention can be carried out. The perimeter consists essentially of a stimulus generator 1 and a computer 2 for controlling the generator and for assessing the responses to presented stimuli that are received from the patient.

The stimulus generator 1 has a screen 3, which may be hemispherical or have some other suitable shape, and in front of which the patient is seated. The screen is provided with a fixation target, for example in the form of a light-emitting diode which is shining continuously and at which the patient is asked to look throughout the test. The stimulus generator 1 serves to provide well-defined visual stimuli at selected locations on the screen, which should be evenly illuminated. These stimuli can be generated by means of a projection system or by means of fixed light sources (light-emitting diodes or optical fibres) or any other suitable means.

Advantageously, the perimeter also has means 4 for monitoring the patient's fixation of the fixation target, such that stimuli that are presented when the patient is blinking or does not maintain fixation can be sorted out or repeated. The fixation monitoring function may be implemented electronically or with the aid of a TV-camera. Other types of fixation monitoring are of course also possible.

The perimeter further comprises a press button 5, by means of which the patient should give a response each time he perceives a visual stimulus on the screen. Responses may also be obtained by measuring pupillary responses or visually evoked potentials or by any other suitable means. The press button 5 is connected to the computer 2 which assesses every response from the patient and, on the basis thereof, determines the location and the intensity of the next visual stimulus in compliance with a control program stored in the computer. The computer has a memory 6, in which for example the responses to the stimuli are stored. The computer is also provided with an input unit 7, by means of which an operator can supply information to the perimeter, and an output unit 8, by means of which the results of the visual field tests are presented. The input unit 7 may, for example, consist of a keyboard and the output unit 8 of a printer or a display device.

The physical design of the perimeter described above does not differ from that of prior-art perimeters. As will be explained hereinafter, the perimeter of the invention is however operated in a completely new manner, allowing a reduced number of stimulus presentations with the aid of a new control program in the computer.

An example of how a static threshold permitry test can be carried out according to the invention will be described hereinafter. This description will be made with reference to the diagram in FIG. 2 and the flow diagram in FIG. 3. (In the following, test locations are referred to as test points.)

Figure 2:
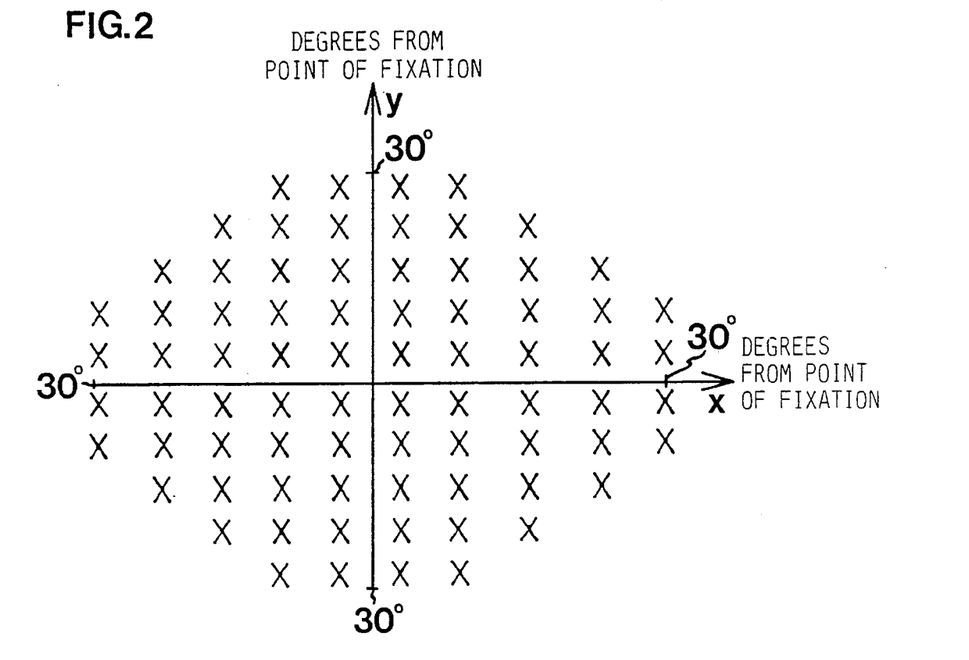
FIG. 2 shows an example of a test pattern.

FIG. 2 shows a test pattern having a number of test points to be tested, each marked with an X, in a coordinate system where both the x-axis and the y-axis indicate the degrees from the point of fixation. The test points are evenly distributed in the four quadrants.

Figure 3:
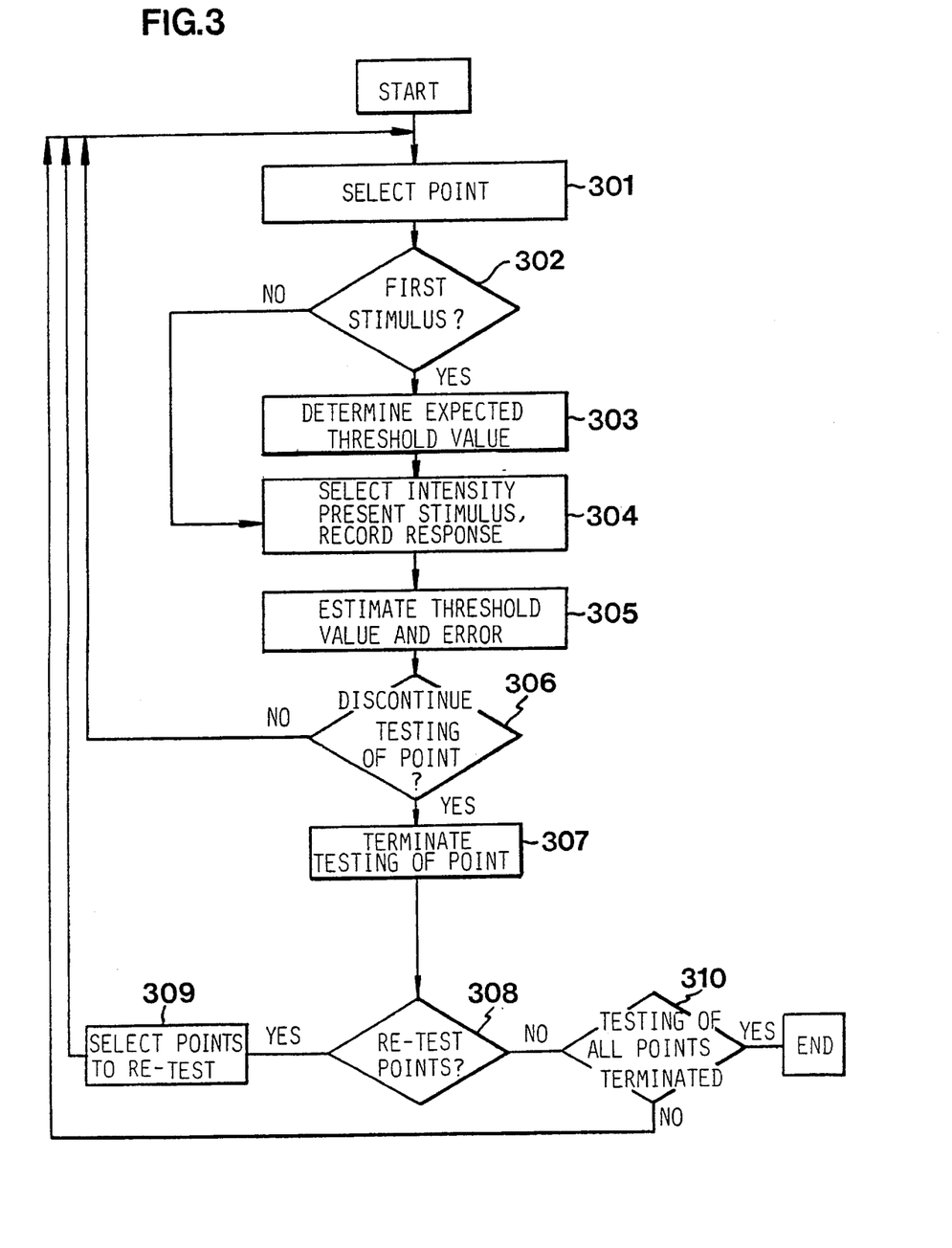
FIG. 3 is a flow diagram of a method for performing a static threshold perimetry test according to the present invention.

According to the flow diagram of FIG. 3 (box 301), one of the points is randomly selected for each stimulus to be presented. When a point has been selected, it is checked whether the stimulus to be presented is the first stimulus presented in the point (box 302). If this is the case, an expected threshold value is calculated for the point (box 303).

When the expected threshold value has been determined, an intensity is selected for the first stimulus to be presented at the point, based on the expected threshold value.

If the stimulus to be presented is not the first stimulus in the point, the intensity value is selected depending on whether the previous stimulus was seen or not seen and on the intensity value of the previous stimulus.

Then, the stimulus of the selected intensity is presented, and it is recorded whether the patient has seen or not seen the presented stimulus on the basis of the patient's response (box 304).

In the next step, the estimated threshold value for the point is calculated as well as the error in the estimated threshold value (box 305). It should be pointed out that both the threshold value and the error are quantitatively calculated, i.e. the magnitude of the threshold value and of the error is determined. How this calculation is done will be described in more detail hereinbelow.

When the threshold value and the error therein have been calculated, it is checked whether the testing of the point is to be discontinued (box 306), the error in the estimated threshold value being used as the criterion therefor. If the testing of the point is not terminated, the program flow returns to box 301 and a new point is selected, which is tested in the same way as described above. If, on the other hand, the testing of the point is to be discontinued, it is terminated.

Towards the end of the test, when the testing of the majority of the points has been terminated and additional information about the visual field has been collected, it may be found that the threshold value estimates for certain test points are not quite satisfactory. It is then advantageous to retest a number of points for which the estimated errors in the threshold value estimates are large. Such test points are tested in the same way as described above. The test program tests (box 308) whether retesting is to be carried out and, if so, selects the points to be retested (box 309). Then, the program flow returns to box 304, and the points that have been selected for retesting are tested together with the remaining points in the manner described above. When the testing of all the points has been terminated (box 310), the test is finished and the final threshold values of all test points may be determined based on all responses received and all intensities of the visual stimuli presented.

It will be described in more detail hereinbelow how the testing of a specific point is carried out with reference to FIG. 4 which shows an example of the testing of a point, where the y-axis indicates the intensity of the stimuli shown and the x-axis indicates the serial number of the stimuli. In the diagram, a ring indicates that the visual stimulus has not been seen, while a cross indicates that it has been seen.

Figure 4:
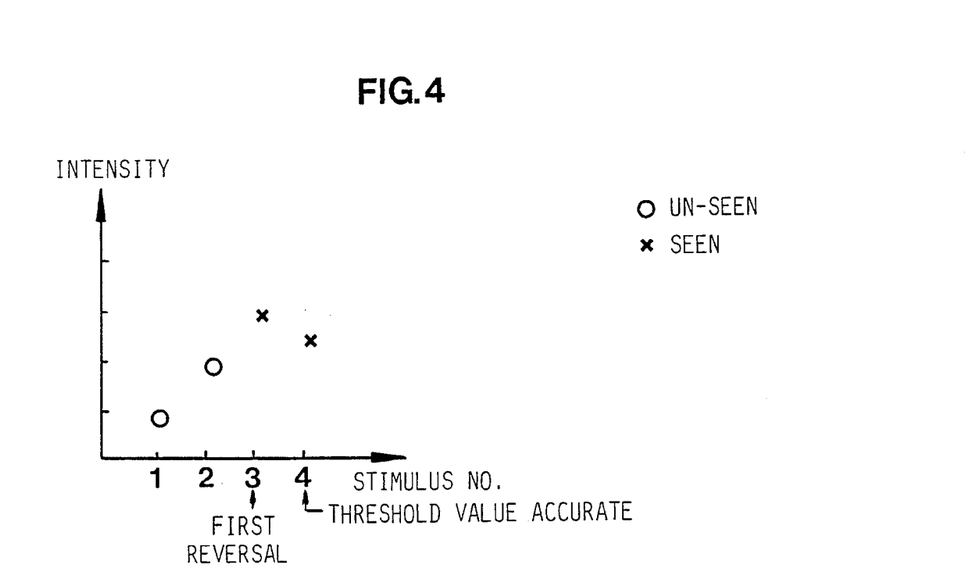
FIG. 4 is a diagram showing an example of stimuli having different intensities presented at a test point.

In the example of FIG. 4, the testing starts by a presentation of stimulus No. 1 having a relatively low intensity. The patient indicates that he does not see this stimulus and therefore stimulus No. 2 is selected to have a higher intensity. Since the patient does not see stimulus No. 2 either, the stimulus intensity is increased further. The patient then sees stimulus No. 3, and the first reversal is thus obtained. Stimulus No. 4 is consequently selected to have a lower intensity than stimulus No. 3, but the difference between stimuli Nos. 3 and 4 is only half the difference between stimuli Nos. 2 and 3. The patient indicates that he has seen stimulus No. 4. Up to this stage of the testing of the point, the estimated error of the threshold value has been large, but after stimulus No. 4 the estimated error of the threshold value for the point is sufficiently small and therefore testing is discontinued, despite the fact that no second reversal has been obtained as is required in most prior-art perimeters.

If the estimated error for the point is not sufficiently small when the second reversal is obtained, the testing of the point may nevertheless be discontinued. Alternatively, a second test sequence may be carried out before the testing is discontinued.

Later on, the point may be retested if the error of the threshold value estimate is large at that stage.

The error may, but need not necessarily, be calculated in connection with each stimulus presentation. Usually, the error is large at the beginning of each test series. Therefore, it may be superfluous to calculate the error in connection with each stimulus presentation in a test series, or at all, until the test series has reached a predetermined state, e.g. until a predetermined number of stimuli have been presented in the test series.

All stimuli presented in the point, i.e. stimulus No. 1–No. 4 and possibly stimuli presented during a retesting sequence, constitute the test series of the point.

In the following it will be explained how threshold values and errors therein can be estimated on the basis of posterior probability functions.

As is well-known, a posterior probability function is a product of a prior probability function and the likelihood function.

The prior probability function indicates a priori known information about a parameter which is to be estimated. In this case, the prior probability function specifies how common different threshold values are in a specific population of subjects.

The likelihood function indicates the probability of obtaining a specific set of values in a random sample of a random variable, the distribution of which depends on an unknown parameter. In this case, the likelihood function specifies the probability of obtaining a specific series of responses (seen/unseen) for a specific series of stimulus intensities, the unknown parameter being the threshold value.

The posterior probability function may be used to estimate the threshold values. One possibility of doing this is to find the threshold values which maximize the posterior probability function and to use these as threshold estimates. However, this is rather complicated and requires a lot of computation time. An easier way is to find the threshold values which sequentially maximize the conditional posterior probability at each point, given the current values of all other points. The conditional posterior probability is defined as follows:

$$P(A|B) = \frac{P(A \text{ and } B)}{P(B)} \quad (1)$$

where A contains the value of the point under study and B contains the values of all other points. This method is called Iterated Conditional Modes or ICM. One version of it is described in Besag, J. E., (1986), On the statistical analysis of dirty pictures, J. Roy. Stat. Soc. B 48, pp 259–302.

According to the preferred embodiment of the invention, the conditional posterior probability function can be expressed as:

$$g_i(s_i, t_i) = l_i(s_i, t_i) \, p_i(s_i) f_i(s_i, t_i) \quad (2)$$

where $g_i$ is the conditional prosterior probability of point i, $t_i$ is the threshold value of point i and $s_i$ is the defect status variable, which can be +1 or −1, of point i. The defect status indicates whether the point is a normal point (+1) or a defective point (−1).

Furthermore, $l_i(s_i, t_i)$ in formula (3) is the likelihood function of point i, which can be expressed as:

$$l_i(s_i, t_i) = \quad (3)$$

$$\left\{ \prod_{q=1;\,\text{response}}^{N_i} \left( FP + (1 - FN - FP)\Phi\left(\frac{-d_q + t_i}{Sd_i}\right) \right) \right\} \times$$

$$\left\{ \prod_{q=1;\,\text{response}}^{N_i} \left( 1 - FP - (1 - FN - FP)\Phi\left(\frac{-d_q + t_i}{Sd_i}\right) \right) \right\}$$

where FP is the frequency of false positive responses, FN the frequency of false negative responses $N_i$ the number of stimuli presented at the i:th point, $d_q$=the q:th stimulus intensity, $\phi$ is the standard normal distribution function and $Sd_i$ is the standard deviation at the i:th point.

Furthermore, $p_i(s_i)$ in formula (3) is the conditional prior defect status probability of point i, which is expressed as $$p_i(s_i) = \exp\left\{ s_i \left( \sum_{j \in n_i^s} \beta_{i,j} s_j \right) / 2 \right\} \quad (4)$$

where $n_i^s$ is the number of nearest neighbors regarding defect status to point i and $\beta_{ij}$ is a parameter which measures the dependence between points i and j.

Moreover, $f_i(s_i, t_i)$ in formula (3) is the conditional prior density of the threshold values and can be expressed as $$f_i(s_i, t_i) = \quad (5)$$

$$\frac{1}{\sigma_i(s_i)\sqrt{2\pi}} \exp\left\{ -\frac{1}{2\sigma_i^2(s_i)} (t_i - \mu_i(s_i) - c\sigma(s_i)\bar{d}_i(s))^2 \right\}$$

where c is a constant. Moreover, $\mu_i(s_i)$ is either $\mu_i(+1)$ or $\mu_i(-1)$. $\mu_i(+1)$ is the normal age-corrected threshold value of point i and $\mu(-1)$ is the defective age-corrected threshold value thereof. Furthermore, $\bar{d}_i(s)$ is the mean value of the standardized deviations of the neighboring points.

As mentioned above, the threshold values can be estimated by maximizing the conditional probability by means of the Iterated Conditional Modes method. According to the ICM-method, the test points are visited sequentially.

For each visit, two maxima are calculated. To obtain the first one, $s_i$ is set at +1, and $g_i (+1, t_i)$ is maximized. This maximum is denoted $g_i (+1, t_{+1}^*)$, where $t_{+1}^*$ is the threshold value which maximizes $g_i (+1, t_i)$. To obtain the second maximum, $s_i$ is set at −1 and $g_i(-1, t_i)$ is maximized. The second maximum is denoted $g_i (-1, t_{-1}^*)$.

If $g_i (+1, t_{+1}^*)$ is greater than $g_i (-1, t_{-1}^*)$ the defect status estimate s* is set at +1, and otherwise at −1.

When the visit to a point is finished, the threshold value of the point is updated to $t^*_{s^*}$ and its defect status value to s*.

When all points have been visited a few times, the threshold values will converge and the thus-established threshold values can be used as threshold estimates.

A point is visited by the ICM-method before and after a stimulus is presented at the point, and after a stimulus has been presented at a neighboring point. Points are also visited in scans. In a scan, all test points are visited once and the conditional posterior probability is maximized pointwise. Preferably, a scan is performed in connection with each stimulus presentation, but other intervals between scans are also conceivable.

When the testing of all points has been terminated, the ICM-method is used to determine the final threshold values of all points.

The error of the threshold estimates can be estimated by calculating the pointwise variance of the posterior probability function. However, the threshold error E may be approximated as follows:

$$E = \sqrt{\left[-\frac{d^2}{dt^2} \ln(g_i(s^*, t^*_{s^*}))\right]^{-1}} \quad (6)$$

In the preferred embodiment, the threshold error is calculated at the currently best threshold value estimate. However, it is not mandatory to use the currently best threshold estimate. In some cases, the error may be calculated using the intensity of e.g. the last stimulus of the point as an estimate of the threshold value and still provide a good estimation of the accuracy of a threshold value determination based on testing made so far for the point.

Furthermore, the magnitude of the error is not necessarily the only criterion for judging whether the point should be further tested or not. One or more of the following values may also be used:

$\Delta$logapo=$\ln(g_i(s^*,t_{s^*}*))-\ln(g_i(s^*,t_{-s^*}*))$ $\Delta$thr=$t_{s^*}*-t_{-s^*}*$ thr=$t_{s^*}*$, thr=the number of thresholding sequences done in a test series rev=the number of reversals maxtrip=the difference in strength between the first and the last stimulus of the point The result of the test is usually presented in one or more maps. In one map, the threshold values may be numerically presented at the respective test locations. In another map, the threshold values may be presented by gray-scale representation. In a further map, the deviation of each threshold value from the normal expected value at its test location may be numerically presented. In still another map, the significances of the deviations may be presented by gray-scale respresentation. The information in the maps enables a physician to diagnose glaucome and other eye diseases and to decide on the treatment thereof.

The results of other visual tests may be presented in similar ways.

The computerized perimeter shown in FIG. 1 preferably has a control program for controlling the perimeter for operation according to the method described above. Such a control program can be achieved by those skilled in the art on the basis of the embodiment described above and, therefore, will not be discussed in more detail here.

The currently preferred embodiment of the invention has been described in the foregoing. Many modifications are however conceivable within the scope of the appended claims.

The method according to the invention is not restricted to be used in accordance with the staircase method. It is equally useful in accordance with the MOBS method, the Robbins-Monroe method or any other method which aims at finding the threshold values.

The method according to the invention may, but need not necessarily, be used for all the test points.

Other types of prior probability functions may be used. For example, one may choose to have a prior probability function identically equal to 1 for determining the error in the threshold value estimates. In this case, the method corresponds to Maximum Likelihood estimation. It is also conceivable to use other types of likelihood functions. The normal distribution function can be replaced with a logistic distribution function or any other distribution function. The likelihood function may also have a more complicated form than a product, e.g. if the responses are dependent.

One alternative way of estimating the error is to calculate an error index EI according to the following formula:

$EI=a \cdot thr+b \cdot \#thr+c \cdot thrn+d \cdot sdn$ where a, b, c and d are constants, thr is a threshold value estimate, #thr is defined above, thrn is the mean value of the threshold values of the neighbor points, and sdn is the standard deviation of the threshold values of the neighbor points.

It is not mandatory to use probability functions that contain defect status.

Furthermore, the error and the threshold estimates may also be used for selecting the strength of a subsequent stimulus in a test series. If the error is great, the difference in strength between successive stimuli in a test series may be larger than if the error is small.

What we claim and desire to secure by Letters Patent is:

1. A method of checking the thresholds of a subject's perception of visual stimuli, each stimulus having a selected strength and belonging to one of a plurality of test series, comprising, for each one of a selection of the test series, the steps of:

presenting at least one visual stimulus;

recording for said at least one visual stimulus any response thereto from the subject;

estimating the value of the error of a threshold value estimate of the test series based on said any response or absence thereof from the subject and the strength of said at least one visual stimulus, and using said value of the error to judge whether the test series is to be continued or not.

2. A method according to claim 1, wherein a posterior probability function is used for estimating said value of the error of the threshold value estimate.

3. A method according to claim 1, wherein said step of estimating the value of the error is performed in connection with each presentation of a visual stimulus, when the test series has reached a predetermined state.

4. A method according to claim 1, further comprising the step of obtaining said threshold value estimate by means of a posterior probability function.

5. A method according to claim 1, further comprising, for each one of said selection of the test series, the step of estimating a threshold value for the test series when the test series has been discontinued, the threshold value estimation being based on said any response or absence thereof from the subject and the strength of said at least one visual stimulus.

6. A method according to claim 5, wherein the step of estimating a threshold value for the test series is performed when all the test series have been discontinued.

7. A method according to claim 1, wherein the strength of a visual stimulus is selected based on a threshold value estimate of the test series to which the visual stimulus belongs.

8. A method according to claim 1, wherein the strength of a visual stimulus is selected based on the estimated error value of a threshold value estimate of the test series to which the visual stimulus belongs.

9. A method according to claim 1, wherein stimuli belonging to different test series are presented at different test locations.

10. A method according to claim 1, wherein stimuli belonging to different test series have different appearances.

11. A method according to claim 1, further comprising the steps of:

classifying said at least one visual stimulus as "seen" or "not seen";

reducing the strength of subsequently presented visual stimuli if said at least one visual stimulus is classified as "seen";

increasing the strength of subsequently presented visual stimuli if said at least one visual stimulus is classified as "not seen";

reversing from decreasing the strength to increasing it for the subsequent visual stimuli if the latest but one stimulus is classified as "seen", but the latest as "not seen";

reversing from increasing the strength to decreasing it for the subsequent visual stimuli if the latest but one stimulus is classified as "not seen", but the latest as "seen";

and wherein said step of using the value of the error comprises the step of discontinuing the test series when said value of the error is less than a predetermined value or when a predetermined number of reversals have been made.

12. A method according to claim 11, further comprising, after a predetermined number of the test series have been discontinued, the steps of restarting at least one discontinued test series, said discontinued test series being selected on the basis of the value of the error of the threshold value estimate of the test series.

13. A method of determining the threshold values of a subject's perception of visual stimuli, comprising the steps of:

successively presenting visual stimuli, each having a selected intensity and being presented at a selected test location;

recording, for each visual stimulus, any response thereto from the subject;

estimating, for each location, a threshold value and a value of the error of the threshold value by means of a posterior probability function;

discontinuing the testing of a test location when the threshold value estimate is deemed to be accurate based on the value of the error thereof;

retesting at least one test location, the value of the error of which, when the testing of a predetermined share of the test locations has been discontinued, exceeds a predetermined value;

determining, when the testing of all test locations has been discontinued, a threshold value for each of the test locations by means of a posterior probability function and based on the intensities of the visual stimuli presented and the responses and absences of responses thereto.

14. A method of checking the thresholds of a subject's perception of visual stimuli, each stimulus having a selected strength and belonging to one of a plurality of test series, comprising, for each one of a selection of the test series, the steps of:

presenting at least one visual stimulus;

recording for said at least one visual stimulus any response thereto from the subject;

classifying said at least one visual stimulus as "seen" or "not seen";

reducing the strength of the subsequently presented visual stimulus if said at least one visual stimulus is classified as "seen";

increasing the strength of the subsequently presented visual stimulus if said at least one visual stimulus is classified as "not seen"; and estimating the value of the error of a threshold value estimate of the test series based on said any response from the subject and the strength of said at least one visual stimulus.

15. An apparatus for checking the thresholds of a subject's perception of visual stimuli, comprising means for presenting visual stimuli, each having a selected strength and belonging to a selected test series;

memory means for storing the responses from the subject to the stimuli; and a control unit which, for at least one test series, is adapted to perform the operations of presenting at least one visual stimulus;

recording for said at least one visual stimulus any response thereto from the subject;

estimating the value of the error of a threshold value estimate of the test series based on said any response or absence thereof from the subject and the strength of said at least one visual stimulus, and using said value of the error to judge whether the test series is to be continued or not.

16. An apparatus according to claim 15, wherein the control unit is adapted to use a posterior probability function for estimating said value of the error of the threshold value estimate.

17. An apparatus according to claim 15, wherein the control unit is adapted to obtain said threshold value estimate by means of a posterior probability function.

18. An apparatus according to claim 15, wherein the control unit is further adapted to classify said at least one visual stimulus as "seen" or "not seen";

reduce the strength of subsequently presented visual stimuli if said at least one visual stimulus is classified as "seen";

increase the strength of the subsequently presented visual stimuli if said at least one visual stimulus is classified as "not seen";

reverse from decreasing the strength to increasing it for the subsequent visual stimuli if the latest but one stimulus is classified as "seen", but the latest as "not seen";

reverse from increasing the strength to decreasing it for the subsequent visual stimuli if the latest but one stimulus is classified as "not seen", but the latest as "seen";

discontinue the test series when said value of the error is less than a predetermined value or when a predetermined number of reversals have been made.

19. An apparatus for determining the threshold values of a subject's perception of visual stimuli, comprising means for successively presenting visual stimuli, each having a selected intensity and being presented at a selected test location;

means for recording, for each visual stimulus, any response thereto from the subject;

means for estimating, for each location, a threshold value and a value of the error of the threshold value by means of a posterior probability function;

means for discontinuing the testing of a test location when the threshold value estimate is deemed to be accurate based on the value of the error thereof;

means for retesting at least one test location, the value of the error of which, when the testing of a predetermined share of the test locations has been discontinued, exceeds a predetermined value;

means for determining, when the testing of all test locations has been discontinued, a threshold value for each of the test locations by means of a posterior probability function and based on the intensities of the visual stimuli presented and the responses and absences of responses thereto.

20. An apparatus for checking the thresholds of a subject's perception of visual stimuli, comprising means for successively presenting visual stimuli, each having a selected strength and belonging to a selected test series;

means for recording responses to visual stimuli from the subject;

means for classifying visual stimuli as "seen" or "not seen";

means for selecting the strengths of visual stimuli based on the classification of previously presented stimuli; and means for estimating values of the errors of threshold estimates of the test series based on the responses and absences of responses from the subject and the strengths of the visual stimuli presented.

* * * * *